US005919672A

United States Patent [19]

Homann et al.

[11] Patent Number: 5,919,672

[45] Date of Patent: Jul. 6, 1999

[54] RESOLUTION OF TRANS-2-(ALKOXYCARBONYLETHYL)-LACTAMS USEFUL IN THE SYNTHESIS OF 1-(4-FLUORO-PHENYL)-3(R)-[(S)-HYDROXY-3-(4-FLUOROPHENYL)-PROPYL]-4(S)-(4-HYDROXYPHENYL)-2-AZETIDINONE

[75] Inventors: Michael J. Homann, Clinton; William Brian Morgan, Chatham, both of N.J.

[73] Assignee: Schering Corporation, Kenilworth, N.J.

[21] Appl. No.: 09/165,951

[22] Filed: Oct. 2, 1998

[51] Int. Cl.[6] .............................. C12P 17/10; C12P 41/00

[52] U.S. Cl. .......................... 435/121; 435/170; 435/171; 435/197; 435/280; 435/822; 435/872; 435/874; 435/886; 435/911; 435/913; 435/917; 435/921; 435/931; 435/933

[58] Field of Search .................................... 435/121, 170, 435/171, 197, 280, 822, 872, 874, 886, 911, 913, 917, 921, 931, 933

[56] References Cited

U.S. PATENT DOCUMENTS

| | | | |
|---|---|---|---|
| 5,317,100 | 5/1994 | Kalvoda et al. | 435/121 |
| 5,618,707 | 4/1997 | Homann et al. | 436/146 |
| 5,767,115 | 6/1998 | Rosenblum et al. | 514/210 |

*Primary Examiner*—Herbert J. Lilling
*Attorney, Agent, or Firm*—Anita W. Magatti

[57] ABSTRACT

A process for the microbiological or enzymatic hydrolytic resolution of racemic trans-2-(alkoxycarbonylethyl) lactams of the formula I:

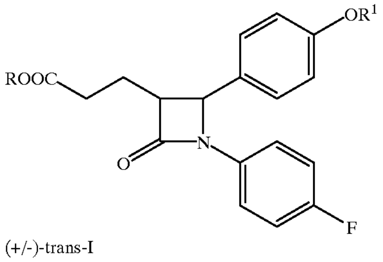

(+/-)-trans-I wherein R is $C_1$–$C_7$ alkyl, 2,2,2-trifluoroethyl or methoxy-ethoxyethyl and $R^1$ is hydrogen or a protecting group is disclosed, whereby an optically enriched compound of the formula Ib or IIa:

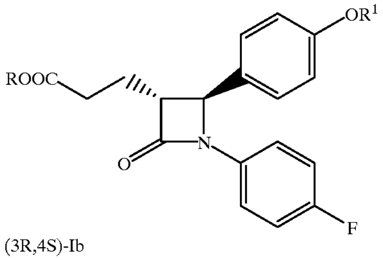

(3R,4S)-Ib

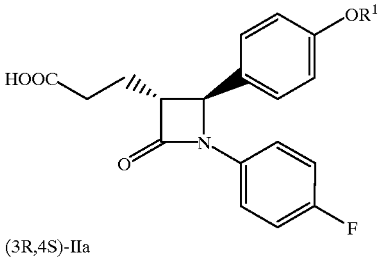

(3R,4S)-IIa is obtained.

18 Claims, No Drawings

RESOLUTION OF TRANS-2-(ALKOXYCARBONYLETHYL)-LACTAMS USEFUL IN THE SYNTHESIS OF 1-(4-FLUORO-PHENYL)-3(R)-[(S)-HYDROXY-3-(4-FLUOROPHENYL)-PROPYL]-4(S)-(4-HYDROXYPHENYL)-2-AZETIDINONE

BACKGROUND OF THE INVENTION

Trans-2-(alkoxycarbonylethyl)lactams and trans-2-(carboxyethyl)lactams are intermediates in the synthesis of 1-(4-fluorophenyl)-3(R)-[3(S)-hydroxy-3-(4-fluorophenyl)-propyl)]-4(S)-(4-hydroxyphenyl)-2-azetidinone, a cholesterol lowering agent disclosed in U.S. Pat. No. 5,767,115.

U.S. Pat. No. 5,618,707 discloses stereoselective microbial reduction of a keto intermediate (4-(4-fluoro-benzoyl) butyric acid or a phenyloxazolidinone conjugate thereof) to the corresponding hydroxy intermediate used in the preparation of the azetidinone. Preferred microorganisms used in the process are *Zygosaccharomyces bailii* or *Schizosaccharomyces octosporus.*

SUMMARY OF THE INVENTION

The process of the present invention relates to microbiological or enzymatic hydrolytic resolution of a racemic trans-2-(alkoxycarbonylethyl)lactam of the formula I:

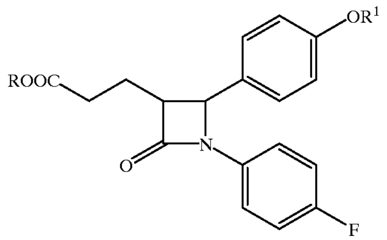

(+/-)-trans-I wherein R is $C_1$–$C_7$ alkyl, 2,2,2-trifluoroethyl or methoxyethoxyethyl and $R^1$ is hydrogen or a protecting group selected from the group consisting of benzyl, trimethylsilyl, t-butyldimethylsilyl (TBDMS) and acetyl, to obtain an optically enriched compound of the formula Ib or IIa:

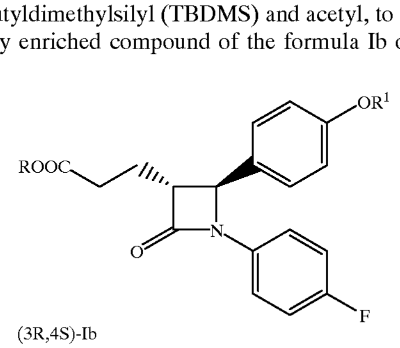

(3R,4S)-Ib

-continued

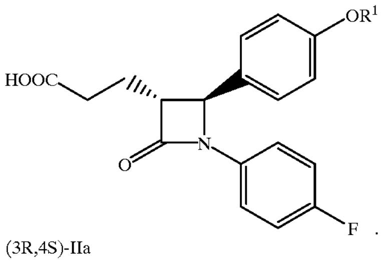

(3R,4S)-IIa

When a carboxylic acid ester of formula Ib is obtained, the process further comprises hydrolysis of the resulting compound of formula Ib to obtain an acid of formula IIa. The resulting 3R,4S lactam acid is useful as an intermediate in the preparation of 1-(4-fluorophenyl)-3(R)-[3(S)-hydroxy-3-(4-fluorophenyl)propyl)]-4(S)-(4-hydroxyphenyl)-2-azetidinone.

The resolution comprises the use of microorganisms (obtained from environmental sources and culture collections, e.g., the American Type Culture Collection (ATCC)) in medium, medium and buffer, medium and solvent, or medium and a mixture of buffer and solvent, or the use of enzymes in buffer, solvent or a mixture thereof, to which a racemic trans-2-(alkoxycarbonylethyl)lactam is added so that a compound having an ester or acid group of desired stereochemistry can be formed, accumulated and isolated. The resolution is either direct or subtractive, depending on the microorganism or enzyme used.

Microorganisms selected from the group consisting of the following genera have been found to be useful in the direct resolution: Aspergillus, Bacillus, Candida, Cunninghamella, Debaryomyces, Mycobacterium, Paecilomyces, Penicillium, Rhodobacter, Streptomyces and Trichothecium. The following species of the above genera are preferred: *Aspergillus alliaceus, niger, niveus* and *terreus; Bacillus sphaericus; Candida parapsilosis* and *rugosa; Cunninghamella homothallica; Debaryomyces hansenii; Mycobacterium fortuitum; Paecilomyces marquandii; Penicillium implicatum; Rhodobacter sphaeroides; Streptomyces spectabilis*; and *Trichothecium roseum.*

Microorganisms selected from the group consisting of the following genera have been found to be useful in the subtractive resolution: Comamonas, Curvularia, Mucor, Nocardia and Rhodococcus. The following species of the above genera are preferred: *Comamonas testosteroni; Curvularia brachyspora* and *geniculata; Mucor circinelloides* and *racemosus; Nocardia corallina*; and *Rhodococcus erythropolis, rhodochrous* and species.

Commercially available enzymes suitable for use in the resolution of this invention include Amano Lipase D (*Rhizopus delemar*); Amano Lipase FAP-15 (*Rhizopus javanicus*); Amano Lipase MAP-10 (*Mucor javanicus*); Amano Lipase N (*Rhizopus niveus*); Interspex Bacterial Esterase/Lipase BE1-Supported (*Pseudomonas mandocino*); Nagase Lipase A-10 (*Rhizopus japonicus*); Novo SP 525 (*Candida antarctica*, type B); Toyobo Lipoprotein lipase LPL-701 and LPL-311, type A (Pseudomonas sp.); Seikagaki Lipase (*Rhizopus delemar*); Kinzi & Payne Lipase WT (Rhizopus sp.); Svedas Lipase (*Rhizopus oryzae*); Sawa Lipase A-10 (*Rhizopus japonicus*); Sawa LPL-701 and LIP 301 (Pseudomonas sp.); Boehringer-Mannheim Chirazyme™ L2 (*Candida antarctica* lipase, type B); Boehringer-Mannheim Chirazyme™ L4 and L6 (Pseudomonas sp.); Interspex Lipase/Esterase ICS-16-FL1 Fungal (*Rhizopus oryzae*); Fluka Lipase (*Aspergilius niger*);

Toyobo LIP-300/301 and LIP-321 (Pseudomonas sp.); Toyobo Lipoprotein lipase LPL 311 Type A (Pseudomonas sp.); Novo Lipozyme IM-60 (*Mucor miehei*); and Sigma Lipase Type XI (*Rhizopus arrhizus*).

Preferred enzymes are hydrolases of Pseudomonas sp. (Toyobo LPL 311 Type A, Toyobo LIP-301/LIP 300, Toyobo LPL 701, Boehringer-Mannheim Chirazyme™ L6).

In particular, the present invention relates to direct resolution of trans-1-(4-fluorophenyl)-3-(alkoxycarbonylethyl)]-4(S)-(4-hydroxyphenyl)-2-azetidinone comprising adding said compound to a microorganism in medium, medium and buffer, medium and solvent, or medium and a mixture of buffer and solvent, especially wherein the microorganism is *Aspergillus terreus* or *alliaceus*, or *Candida parapsilosis*, incubating the resulting mixture, and isolating a compound of the formula IIa

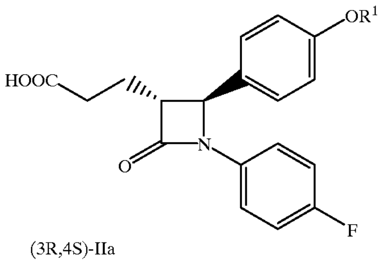

(3R,4S)-IIa wherein $R^1$ is as defined above.

In particular, the present invention also relates to subtractive resolution of trans-1-(4-fluorophenyl)-3-(alkoxycarbonylethyl)]-4(S)-(4-hydroxy-phenyl)-2-azetidinone comprising adding said compound to a microorganism in medium, medium and buffer, medium and solvent, or medium and a mixture of buffer and solvent, especially wherein the microorganism is *Rhodococcus rhodochrous* or Rhodococcus species, or to an enzyme in a solvent, buffer or a mixture thereof, especially wherein the enzyme is a hydrolase from Pseudomonas sp., incubating the resulting mixture, and isolating a compound of the formula Ib:

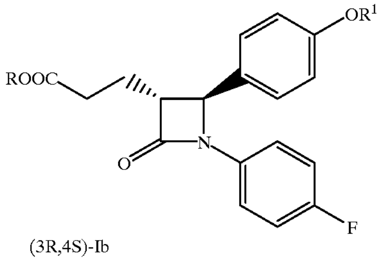

(3R,4S)-Ib wherein R and $R^1$ are as defined above. The compound of formula Ib is then hydrolysed to remove the carboxylic acid ester group, R, to obtain a compound of formula IIa.

DETAILED DESCRIPTION

The hydrolytic resolution of the present invention is summarized in the following reaction scheme:

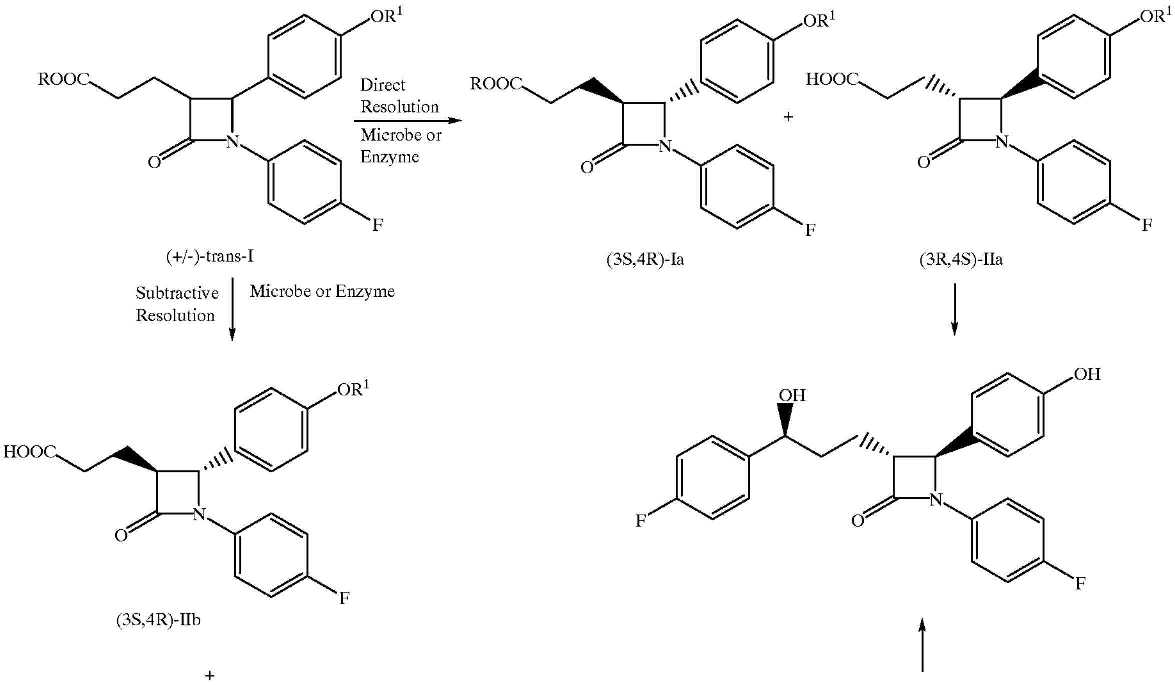

(+/-)-trans-I (3S,4R)-Ia

+

(3R,4S)-IIa (3S,4R)-IIb

+

-continued

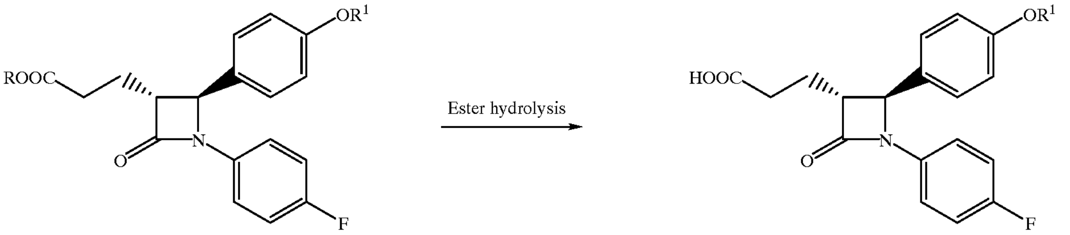

(3R,4S)-Ib (3R,4S)-IIa

This scheme shows a method for performing a direct hydrolysis using a microorganism or enzyme, where racemic lactam ester I is hydrolyzed to generate enantiomerically enriched acid (3R,4S)-IIa which is easily separated from unreacted carboxylic acid ester (3S,4R)-Ia. Alternatively, a subtractive resolution of racemic lactam ester I yields acid IIb and enantiomerically enriched carboxylic acid ester (3R,4S)-Ib which is subsequently hydrolyzed to generate (3R,4S)-IIa. The enantiomerically enriched (3R,4S)-IIa is subsequently used to synthesize 1-(4-fluorophenyl)3(R)-[3(S)-hydroxy-3-(4-fluorophenyl) propyl)]-4(S)-(4-hydroxy-phenyl)-2-azetidinone using procedures known in the art, for example by converting the acid of formula IIa to the corresponding acid chloride, reacting the acid chloride with a 4-fluorophenyl derivative, and reducing the ketone to the alcohol as described in Method H of U.S. Pat. No. 5,767,115.

The hydrolytic resolution is carried out by adding a racemic trans-2-(alkoxycarbonylethyl) lactam I to medium, medium and buffer, medium and solvent, or medium and a mixture of buffer and solvent containing microorganisms, or to solvent, buffer, or a mixture thereof, containing enzymes. The bioconversion may be conducted at temperatures in the range from between about 20° C. to about 40° C.; the microbial reaction is preferably conducted at ambient temperature to 30° C. and the enzymatic reaction is preferably conducted at ambient temperature to 37° C. The initial pH value of the reaction is adjusted to be in the range from between about pH 5.0 to about 9.0, preferably pH 7.0.

The initial concentration of racemic trans lactam ester I in the microbial reaction may vary from between about 0.5 g/l to about 5 g/l, and is preferably 0.5 g/l. The duration of the microbial hydrolysis may vary from about 18 to about 96 hours, and is preferably about 48 hours.

The initial concentration of trans lactam ester I in the enzyme mediated reaction may vary from between about 5 mg/ml to about 200 mg/ml, and is preferably 25 mg/ml. The duration of the enzymatic hydrolysis may vary from about 24 to about 192 hours.

Suitable fermentation media, buffers and solvents are known to those skilled in the art. Fermentation media typically contain a carbon and nitrogen source or mixtures thereof, using such ingredients as yeast extract, nutrient broth, dextrose (cerelose), white potato dextrin, soy flour, peptone and other components known in the art. Typical buffers are phosphate buffer (e.g., 0.1 M at pH 7), MES (2-[N-morpholino]ethanesulfonic acid), Bis-Tris (bis[2-hydroxyethyl]iminotris[hydroxymethyl]methane), PIPES (1,4-piperazine-diethanesulfonic acid), HEPES (N-[2-hydroxyethyl]piperazine-N'-[2-ethanesulfonic acid]), TRIS (tris(hydroxymethyl)aminomethane) and MOPS (3-[N-morpholino]propanesulfonic acid) buffer (e.g., 0.1 M at pH 7). Typical solvents are acetonitrile, acetone, ethyl ether, isopropanol, t-butanol, isoamyl alcohol, p-dioxane, isopropyl ether, dimethyl sulfoxide, t-butyl methyl ether (TBME), toluene, tetrahydrofuran and $CH_2Cl_2$. Preferably, the microbial resolutions are carried out in fermentation media, and the enzymatic resolutions preferably are carried out in a buffer with a co-solvent; a preferred co-solvent for enzymatic resolutions is TBME.

At the end of the hydrolysis, optically enriched acids or esters may be extracted using organic solvents such as ethyl acetate (EtOAc), TBME, $CH_2Cl_2$ and the like. Adsorption to resins, chromatography, and other physical methods known in the art may also be used for the isolation of optically enriched acids or esters.

The carboxylic acid ester of formula Ib can be hydrolysed to the corresponding acid of formula IIa using methods well known in the art, for example by treatment with a suitable base, e.g., LiOH, as described in U.S. Pat. No. 5,767,115.

The examples below demonstrate the evaluation of microorganisms and enzymes in the hydrolysis of this invention and the preparation of milligram quantities of compounds of formulas IIa and Ib.

EXAMPLE 1

The general method for identifying the microbial hydrolysis of racemic trans lactam methyl ester I for use in generating acid IIa is described below.

Seed cultures of yeast, filamentous fungi, and bacteria were grown in 125 ml or 300 ml flasks containing 25 ml or 50 ml of YPD (1% yeast extract, 2% peptone, 2% dextrose; pH 5.5), SIM6 (3.5% soy flour, 5% white potato dextrin, 0.5% cerelose, 2 mg/l cobalt chloride, 0.5% calcium carbonate; pH 6.0) and NYC (0.8% nutrient broth, 2% yeast extract, 2% cerelose; pH 7.0) media respectively, for 72 hours at 30° C. with agitation (175–250 rpm) prior to inoculation (4% v/v) into flask fermentations (25 ml YPD/125 ml flask for yeast and filamentous fungi or 25 ml NYC/125 ml flask for bacteria) which were incubated at 30° C. with agitation (250 rpm). In all fermentations, medium pH was adjusted prior to inoculation but was not controlled during culture propagation and substrate hydrolysis. Microbial resolution was initiated by adding 0.5 g/l of racemic trans lactam methyl ester I dissolved in ethanol (25 mg/ml), directly to cultures following 24 hours of growth. Samples of fermentation broth were extracted with TBME following 24–72 hours incubation with substrate and were analyzed by reverse-phase HPLC. Preferred cultures demonstrating selective hydrolysis generating acid IIa are summarized in Table 1.

TABLE 1

Direct resolution of racemic trans lactam methyl esters using microorganisms

| Culture | Strain # (ATCC) | Substrate | Product | % ee | % Yield |
|---|---|---|---|---|---|
| *A. terreus* | 10020 | benzyl | benzyl protected | 100 | 9 |
| | 20542 | protected | IIa: (3R, 4S) acid | 91 | 23 |
| | 24839 | racemate I | | 91 | 35 |
| *Penicillium implicatum* | SPR 938* | benzyl protected racemate I | benzyl protected IIa: (3R, 4S) acid | 100 | 6 |
| *Aspergillus niger* | 9029 | unprotected racemate I | IIa: (3R, 4S) acid | 100 | 14 |
| *Aspergillus alliaceus* | 1024 | unprotected racemate I | IIa: (3R, 4S) acid | 100 | 29 |
| *Candida parapsilosis* | 7330 | unprotected | IIa: (3R, 4S) acid | 100 | 29 |
| | 16632 | racemate I | | 100 | 26 |
| | 22019 | | | 100 | 28 |
| | 34078 | | | 100 | 20 |
| *Candida rugosa* | 14830 | unprotected racemate I | IIa: (3R, 4S) acid | 100 | 20 |

*Schering-Plough Research: Biotransformations Culture Collection

EXAMPLE 2

Milligram quantities of acid IIa derived from the microbial hydrolysis of benzyl protected racemic trans lactam methyl ester I was prepared as described below.

Microbial resolution of methyl ester I (0.5 g/l) to generate acid IIa was conducted as described in Example 1 using multiple flask fermentations employing *Aspergillus terreus* strain ATCC #24839. Following 48 hours of incubation, fermentation broths of each of the cultures were pooled prior to centrifugation to separate the cells from the fermentation broth. Cell pellets were pulverized in liquid nitrogen using a mortar and pestle prior to three sequential extractions with TBME (1–2 volumes/wet weight). Fermentation broth was extracted separately with TBME. The TBME extracts contained both the (3R,4S)-acid and the (3S,4R)-ester, each in >99% enantiomeric excess. Anhydrous $MgSO_4$ was added to the TBME extracts to remove residual water, the extracts were filtered and the filtrate concentrated by evaporation. Extract concentrate was subjected to purification by preparative thin layer chromatography employing multiple 10–20 GF silica plates (20 cm×20 cm×1000 micron) and developed with a solution of EtOAc:hexane (50:50). Material comigrating with the desired product was scraped from each of the silica plates, pooled and eluted from the silica with TBME. The eluate was evaporated to yield the (3R, 4S)-acid IIa: 170 mg, 17% yield; 86% enantiomeric excess; $[\alpha]_D^{25}=-13.0°$ (c=0.123, ethanol).

EXAMPLE 3

The general method for identifying the microbial resolution of benzyl protected racemic trans lactam methyl ester I for use in generating ester Ib is described below.

Seed cultures of yeast, filamentous fungi, and bacteria were grown in 125 ml or 300 ml flasks containing 25 ml or 50 ml of YPD (1% yeast extract, 2% peptone, 2% dextrin; pH 5.5), SIM6 (3.5% soy flour, 5% white potato dextrose, 0.5% cerelose, 2 mg/l cobalt chloride, 0.5% calcium carbonate; pH 6.0) and NYC (0.8% nutrient broth, 2% yeast extract, 2% cerelose; pH 7.0) media respectively, for 72 hours at 30° C. with agitation (175–250 rpm) prior to inoculation (4% v/v) into flask fermentations (25 ml YPD/125 ml flask for yeast and filamentous fungi or 25 ml NYC/125 ml flask for bacteria) which were incubated at 30° C. with agitation (250 rpm). In all fermentations, medium pH was adjusted prior to inoculation but was not controlled during culture propagation and substrate hydrolysis. Microbial resolution was initiated by adding 0.5 g/l of racemic trans lactam methyl ester I dissolved in ethanol (25 mg/ml), directly to cultures following 24 hours of growth. Samples of fermentation broth extracted with TBME following 24–72 hours incubation with substrate were analyzed by reverse-phase HPLC. Cultures yielding optically enriched ester Ib are summarized in Table 2.

TABLE 2

Subtractive resolution of racemic trans lactam methyl esters using microorganisms

| Culture | Strain # (ATCC) | Substrate | Product (methylester) | % ee | % Yield |
|---|---|---|---|---|---|
| *R. erythropolis* | 4277 | benzyl | benzyl | 100 | 17 |
| | 11048 | protected | protected | 100 | 17 |
| | 19369 | racemate I | Ib: (3R, 4S) | 100 | 11 |
| *R. rhodochrous* | 29670 | benzyl | benzyl | 100 | 30 |
| | 19150 | protected | protected | 100 | 22 |
| | 29675 | racemate I | Ib: (3R, 4S) | 100 | 24 |
| *R. species* | 19148 | benzyl | benzyl | 100 | 31 |
| | 19071 | protected racemate I | protected Ib: (3R, 4S) | 100 | 31 |
| *C. testosteroni* | 33083 | benzyl protected racemate I | benzyl protected Ib: (3R, 4S) | 100 | 12 |
| *N. corallina* | 31338 | benzyl protected racemate I | benzyl protected Ib: (3R, 4S) | 100 | 11 |

EXAMPLE 4

Milligram quantities of methyl ester Ib derived from the hydrolysis of benzyl protected racemic trans lactam methyl ester I (0.5 g/l) was prepared as described in Example 3 using multiple flask fermentations employing Rhodococcus species ATCC #19071. Following 48 hours of incubation, fermentation broths of each of the flasks were pooled prior to centrifugation to separate the cells from the fermentation broth. Cell pellets were disrupted by sonication prior to three sequential extractions with TBME (1–2 volumes/wet weight). Fermentation broth was extracted separately with TBME. Anhydrous $MgSO_4$ was added to the TBME extracts to remove residual water, the extracts were filtered and the filtrate concentrated by evaporation. Extract concentrate was subjected to purification by preparative thin layer chromatography employing multiple 10–20 GF silica plates (20 cm×20 cm×1000 micron) and developed with a solution of EtOAc:hexane (50:50). Material comigrating with the desired product was scraped from each of the silica plates, pooled and eluted from the silica with TBME. The eluate was evaporated to yield the (3R,4S)-ester; 360 mg, 36% yield; >99% enantiomeric excess; $[\alpha]_D^{25}=-7.5°$ (c=0.133, ethanol).

EXAMPLE 5

The general method for identifying the enzymatic resolution of benzyl protected racemic trans lactam methyl or trifluoroethyl esters I for use in generating optically enriched acid and ester is described below.

Enzyme screening reactions were conducted using a two-phase system of 0.6 ml TBME with 1.0 ml of 0.1 M phosphate buffer (pH 7.0). Enzyme, typically 50–200 mg or 100–200 μL, was added to the suspension followed by 14.4 mg of methyl ester. The mixture was agitated (350 rpm) at room temperature. Some deviations from these reaction conditions were evaluated as indicated in Table 3. Material was recovered by separating the phases by centrifugation and product and unreacted starting material were analyzed by chiral HPLC. Enzymes demonstrating selective hydrolysis of racemic trans lactam methyl ester I yielding acid IIb and ester Ib are summarized in Table 3.

TABLE 3

Enzymatic resolution of benzyl protected racemic trans lactam methyl ester I yielding optically enriched ester Ib and acid IIb.

| Enzyme | Time (hour) | (3S, 4R) IIb $ee_p$ | (3R, 4S) Ib $ee_s$ | Conversion | E |
|---|---|---|---|---|---|
| Amano Lipase D *Rhizopus delemar* | 64.5 | 0.71 | 0.67 | 0.485 | 11 |
| Amano Lipase FAP-15 *Rhizopus javanicus* | 44.25 | 0.76 | 0.49 | 0.392 | 12 |
| Amano Lipase MAP-10 *Mucor javanicus* | 64.5 | 0.68 | 0.39 | 0.364 | 8 |
| Amano Lipase N *Rhizopus niveus* | 64.5 | 0.75 | 0.34 | 0.312 | 10 |
| Interspex Bacterial Esterase/Lipase BE1 -Supported *P. mandocino* | 44.25 | 0.11 | >0.95 | 0.897 | n/d |
| Nagase Lipase A-10 *R. japonicus* | 44.25 | 0.72 | 0.73 | 0.504 | 13 |
| Novo SP 525 Lipase, type B *C. antarctica* | 122 | 0.77 | 0.18 | 0.191 | 9 |
| Toyobo Lipoprotein lipase (LPL-701) *Pseudomonas sp.* | 46.5<br>90* | 0.95<br>0.957 | 0.62<br>0.486 | 0.395<br>0.337 | 68<br>74 |
| Seikagaki Lipase *Rhizopus delemar* | 122 | 0.69 | 0.63 | 0.478 | 10 |
| Toyobo Lipoprotein Lipase (LPL-311) Type A *Pseudomonas sp.* | 46.5<br>90* | 0.97<br>0.975 | >0.97<br>0.709 | 0.507<br>0.421 | n/d<br>165 |
| Kinzie & Payne Lipase WT *Rhizopus sp.* | 138.25 | 0.72 | 0.41 | 0.359 | 9 |
| Svedas Lipase *Rhizopus oryzae* | 119 | 0.70 | 0.73 | 0.511 | 12 |
| Sawa Lipase A-10 *Rhizopus japonicus* | 47 | 0.68 | 0.82 | 0.547 | 13 |
| Sawa LPL-701 *Pseudomonas sp.* | 90* | 0.967 | 0.467 | 0.326 | 93 |
| Boehringer-Mannheim Chirazyme ™ L2, lipase B *Candida antarctica* | 47 | 0.82 | 0.05 | 0.060 | 11 |
| Boehringer-Mannheim Chirazyme ™ L4 *Pseudomonas sp.* | 119 | 0.94 | 0.24 | 0.206 | 38 |
| Boehringer-Mannheim Chirazyme ™ L6 *Pseudomonas sp.* | 47<br>90* | 0.95<br>0.97 | 0.77<br>0.46 | 0.450<br>0.321 | 86<br>103 |
| Interspex Lipase/Esterase ICS-16-FL1Fungal *Rhizopus oryzae* | 119 | 0.73 | 0.64 | 0.465 | 12 |
| Fluka Lipase *Aspergillus niger* | 71 | 0.44 | 0.43 | 0.495 | 4 |
| Novo Lipozyme IM-60 *Mucor miechei* | 141.5 | 0.49 | 0.15 | 0.235 | 3 |
| Sigma Lipase Type XI *Rhizopus arrhizus* | 136.5 | 0.75 | 0.35 | 0.316 | 10 |

*Conditions: Ester (50 mg), Enzyme (50 mg), TBME/Phosphate Buffer (pH 7) (1 mL:1 mL), 300 rpm, RT.
#Conditions: Ester (19 mg), Enzyme (1 mg), Tetrahydrofuran/0.5M MOPS buffer pH 7.0 (0.2/1.0 mL)

A similar procedure was conducted using benzyl protected racemic trans lactam trifluoroethyl ester I. Enzyme reactions were conducted using a two-phase system of 1.0 ml TBME with 1.0 ml of 0.1 M phosphate buffer (pH 7.0). Approximately 50 mg of enzyme and 50 mg of ester were added to the suspension and mixed with agitation (300 rpm) at room temperature for up to 186 hours. Material was recovered by separating the phases by centrifugation and product and unreacted starting material were analyzed by chiral HPLC. Enzymes demonstrating selective hydrolysis of racemic trans lactam trifluoroethyl ester I yielding acid IIb and ester Ib are summarized in Table 4.

TABLE 4

Enzymatic resolution of benzyl protected racemic trans lactam trifluoroethyl ester I yielding optically enriched ester Ib and acid IIb.

| Enzyme | Time hour | (3R, 4S) Ib $ee_s$ | (3S, 4R) IIb $ee_p$ | Conversion | E |
|---|---|---|---|---|---|
| Toyobo LIP-301 *Pseudomonas sp.* | 186 | 0.755 | 0.987 | 0.433 | 360 |
| Toyobo LPL-701 *Pseudomonas sp.* | 48 | 0.713 | 0.774 | 0.480 | 16 |
| Toyobo LPL 311 (Type A) *Pseudomonas sp.* | 48<br>24 | 0.994<br>0.991 | 0.628<br>0.788 | 0.613<br>0.557 | 23<br>44 |
| Boehringer-Mannheim Chirazyme ™ L6 *Pseudomonas sp* | 48 | 0.680 | 0.796 | 0.461 | 18 |

EXAMPLE 6

Milligram quantities of ester Ib derived from the enzymatic resolution of benzyl protected racemic trans lactam methyl ester were prepared as described below.

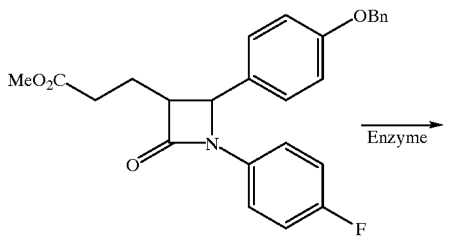

(±)-trans

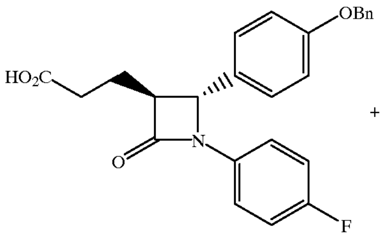

3S,4R

-continued

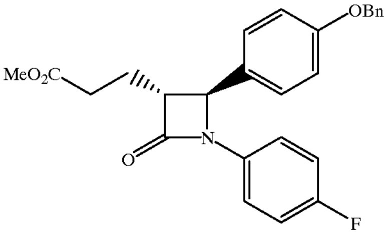

3R,4S

Toyobo LPL-311 (Type A) (Pseudomonas sp.) (202 mg) was dissolved in 0.1M phosphate buffer (pH 7) (8 mL) at room temperature. A solution of racemic methyl ester (199.5 mg, 0.46 mmol) in TBME (8 mL) was added. The two-phase mixture was shaken at 37° C. at 250 rpm for 187 h. The reaction mixture was acidified with 0.5 M $H_2SO_4$ (1 mL), diluted with water (15 mL) and placed in two centrifuge tubes. EtOAc (20 mL) was added to each tube and the tubes shaken, then centrifuged at 3000 rpm for 0.5 h. The organic layer was removed and the extraction/centrifugation repeated twice. The combined organic extracts were evaporated and the crude product was placed on a silica gel column (Selecto 32–63 mesh; 20 g) and eluted with 30% (300 mL) and 50% (400 mL) EtOAc/heptane, collecting fractions of ~20 mL. Fractions 4–6 were combined and evaporated to yield the (3R,4S)-methyl ester: 89 mg, 44.6%; 95.1% enantiomeric excess; $[\alpha]_D^{25}$=−14.15° (c=0.89, ethanol). Fractions 11–19 provided the (3S,4R)-acid: 39 mg, 20.2%; 84.5% enantiomeric excess; $[\alpha]_D^{25}$=+14.87° (c=0.39, ethanol).

EXAMPLE 7

Milligram quantities of acid IIa derived from the enzymatic resolution of benzyl protected racemic trans lactam trifluoromethyl ester, followed by hydrolysis of the trifluoromethyl ester, were prepared as described below.

Step 1

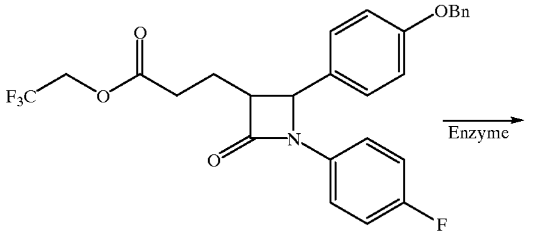

(±)-trans

-continued

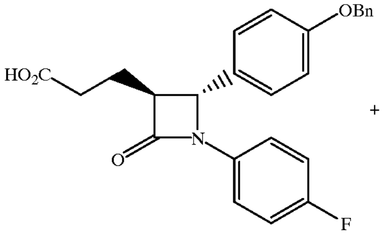

+

3S,4R

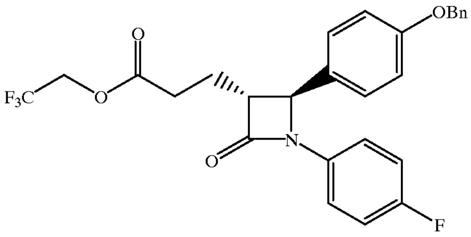

3R,4S

Toyobo LPL-311 (Type A) (Pseudomonas sp.) (365 mg) was dissolved in 0.1M phosphate buffer (pH 7) (16 mL) at room temperature. A solution of racemic trifluorethyl ester (428 mg, 0.85 mmol) in TBME (16 mL) was added. The two-phase mixture was shaken at 37° C. at 250 rpm for 7.75 h, then stored in a refrigerator overnight. The reaction mixture was acidified with 0.5 M $H_2SO_4$ (1 mL), diluted with water (50 mL) and placed in four centrifuge tubes. EtOAc (15 mL) was added to each tube and the tubes shaken, then centrifuged at 3000 rpm for 0.5 h. The organic layer was removed and the extraction/centrifugation repeated twice. The combined organic extracts were evaporated and the crude product was placed on a silica gel column (Selecto 32–63 mesh; 35 g) and eluted with 30% (450 mL) and 50% (600 mL) EtOAc/heptane, collecting fractions of ~20 mL. Fractions 5–7 were combined and evaporated to yield the (3R,4S)-trifluoroethyl ester: 191 mg, 44.6%; 99.0% enantiomeric excess; $[\alpha]_D^{25}$=−9.31° (c=1.88, ethanol). Fractions 18–36 provided the (3S,4R)-acid: 100 mg, 27.9%; 88.3% enantiomeric excess; $[\alpha]_D^{25}$=+15.96° (c=0.99, ethanol).

Step 2

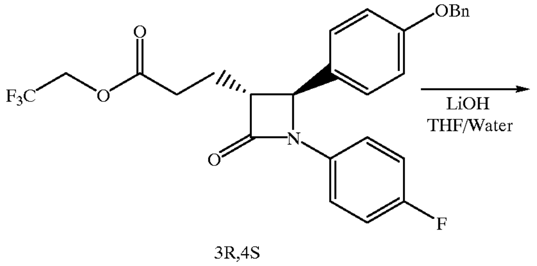

3R,4S

-continued

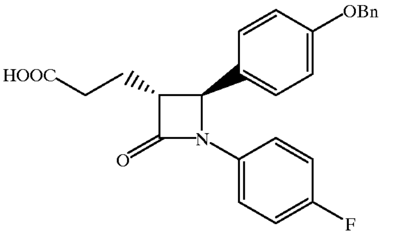

3R,4S (3R,4S)-Trifluoroethyl ester (181 mg, 0.36 mmol) (99.0% ee) was dissolved in THF (4 mL) and cooled to 0° C. in an ice bath. A solution of LiOH (52.5 mg, 1.25 mmol) was added and the mixture stirred at 0° C. for 3.25 h, by which time HPLC indicated complete hydrolysis. The reaction mixture was acidified with 0.5 M $H_2SO_4$ (12 mL) and extracted with EtOAc (2×15 mL). The combined organic extracts were washed with sat'd. NaCl solution (10 mL), dried ($Na_2SO_4$), filtered and evaporated: 146 mg, 96.4%; 98.2% enantiomeric excess.

A sample of the crude product was purified by preparative TLC (Analtech Uniplate Silica Gel GF; 20×20 cm; 1000 μm) eluting with 50% EtOAc/heptane: $[\alpha]_D^{25}$=−16.52° (c=0.66, ethanol).

What is claimed is:

1. A process for the microbiological or enzymatic hydrolytic resolution of a racemic trans-2-(alkoxycarbonylethyl)-lactam of the formula I

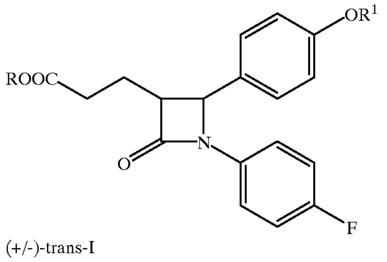

(+/-)-trans-I wherein R is $C_1$–$C_7$ alkyl, 2,2,2-trifluoroethyl or methoxyethoxyethyl and $R^1$ is hydrogen or a protecting group selected from the group consisting of benzyl, trimethylsilyl, t-butyldimethylsilyl and acetyl, comprising:

adding a racemic lactam I to microorganisms in medium, medium and buffer, medium and solvent, or medium and a mixture of buffer and solvent, or to enzymes in buffer, solvent, or a mixture thereof, to obtain an optically enriched compound of the formula Ib or IIa

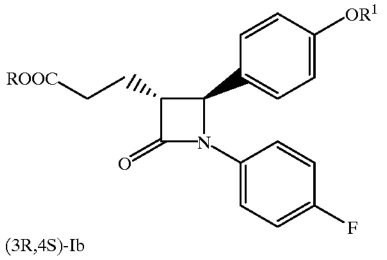

(3R,4S)-Ib

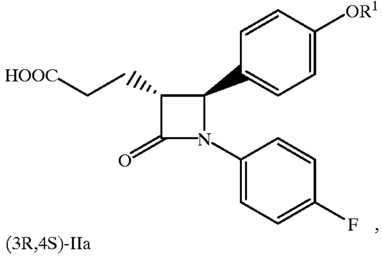

(3R,4S)-IIa

, wherein R and $R^1$ are as defined above; and hydrolysing a carboxylic acid ester of formula Ib to obtain a compound of formula IIa.

2. A process of claim 1 using microorganisms for the resolution of a racemic trans lactam I to obtain optically enriched acid IIa.

3. A process of claim 2 wherein R is methyl.

4. A process of claim 2 wherein the microorganism is of the genera selected from the group consisting of Aspergillus, Bacillus, Candida, Cunninghamella, Debaryomyces, Mycobacterium, Paecilomyces, Penicillium, Rhodobacter, Streptomyces and Trichothecium.

5. A process of claim 4 wherein the microorganism is of the species selected from the group consisting of *Aspergillus alliaceus, niger, niveus* and *terreus; Bacillus sphaericus; Candida parapsilosis* and *rugosa; Cunninghamella homothallica; Debaryomyces hansenii; Mycobacterium fortuitum; Paecilomyces marquandii; Penicillium implicatum; Rhodobacter sphaeroides; Streptomyces spectabilis,* and *Trichothecium roseum.*

6. A process of claim 1 using microorganisms for the resolution of a racemic trans lactam I to obtain optically enriched carboxylic acid ester Ib, followed by hydrolysis to obtain optically enriched acid IIa.

7. A process of claim 6 wherein R is methyl and $R^1$ is benzyl.

8. A process of claim 6 wherein the microorganism is of the genera selected from the group consisting of Comamonas, Curvularia, Mucor, Nocardia and Rhodococcus.

9. A process of claim 8 wherein the microorganism is of the species selected from the group consisting of *Comamonas testosteroni; Curvularia brachyspora* and *geniculata; Mucor circinelloides* and *racemosus; Nocardia corallina*; and *Rhodococcus erythropolis, rhodochrous* and species.

10. A process of claim 1 using enzymes for the resolution of benzyl protected racemic trans lactam I to obtain optically enriched carboxylic acid ester Ib, followed by hydrolysis to obtain optically enriched acid IIa.

11. A process of claim 10 wherein R is methyl or trifluoroethyl and $R^1$ is benzyl.

12. A process of claim 10 wherein the enzyme is selected from the group consisting of a hydrolase from *Rhizopus delemar, Rhizopus javanicus, Mucor javanicus, Rhizopus niveus, Pseudomonas mandocino, Rhizopus japonicus, Candida antarctica,* Pseudomonas sp., Rhizopus sp., *Rhizopus oryzae, Aspergilius niger, Mucor miehei,* and *Rhizopus arrhizus.*

13. A process of claim 12 wherein the enzyme is selected from the group consisting of a hydrolase from a Pseudomonas species.

14. A process for the hydrolytic resolution of a racemic trans-2-(alkoxycarbonylethyl)-lactam of the formula I

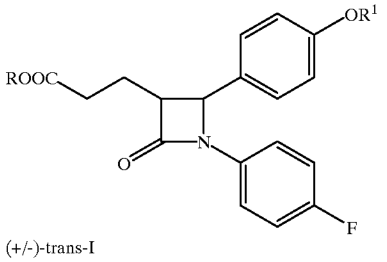

(+/-)-trans-I wherein R is $C_1$–$C_7$ alkyl, 2,2,2-trifluoroethyl or methoxyethoxyethyl and $R^1$ is hydrogen or a protecting group selected from the group consisting of benzyl, trimethylsilyl, t-butyldimethylsilyl and acetyl, comprising:

adding a racemic lactam I to a microorganism of the genera selected from the group consisting of Aspergillus, Bacillus, Candida, Cunninghamella, Debaryomyces, Mycobacterium, Paecilomyces, Penicillium, Rhodobacter, Streptomyces and Trichothecium in medium, medium and solvent, medium and buffer, or medium and a mixture of buffer and solvent, to obtain an optically enriched compound of the formula

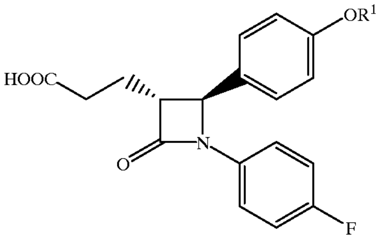

(3R,4S)-IIa wherein $R^1$ is as defined above.

15. A process of claim 14 wherein the microorganism is *Aspergillus alliaceus* or *terreus*, or *Candida parapsilosis.*

16. A process for the hydrolytic resolution of a racemic trans-2-(alkoxycarbonylethyl)-lactam of the formula I

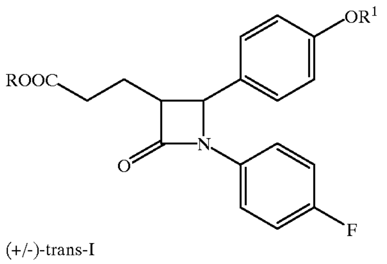

(+/-)-trans-I wherein R is $C_1$–$C_7$ alkyl, 2,2,2-trifluoroethyl or methoxyethoxyethyl and $R^1$ is hydrogen or a protecting group selected from the group consisting of benzyl, trimethylsilyl, t-butyldimethylsilyl and acetyl, comprising:

adding a racemic lactam I to a microorganism of the genera selected from the group consisting of Comamonas, Curvularia, Mucor, Nocardia and Rhodococcus in medium, medium and solvent, medium and buffer, or medium and a mixture of buffer and solvent, to obtain an optically enriched compound of the formula Ib

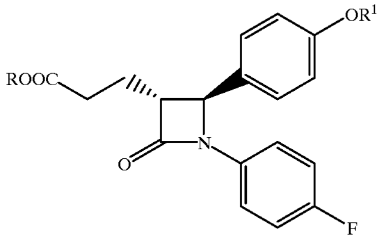

(3R,4S)-Ib wherein R and $R^1$ are as defined above; and hydrolysing the carboxylic acid ester of formula Ib to obtain a compound of formula IIa

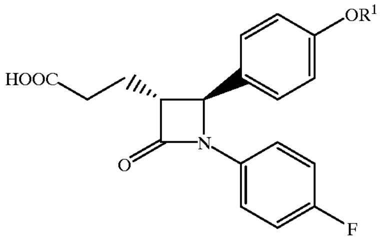

(3R,4S)-IIa wherein $R^1$ is as defined above.

17. A process of claim 16 wherein the micoorganism is *Rhodococcus rhodochrous* or species.

18. A process for the hydrolytic resolution of a racemic trans-2-(alkoxycarbonylethyl)-lactam of the formula I

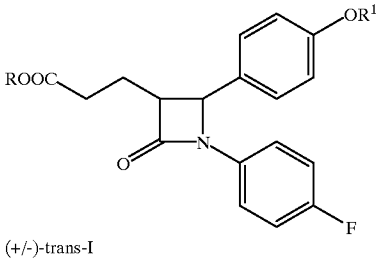

(+/-)-trans-I wherein R is $C_1$–$C_7$ alkyl, 2,2,2-trifluoroethyl or methoxyethoxyethyl and $R^1$ is hydrogen or a protecting group selected from the group consisting of benzyl, trimethylsilyl, t-butyldimethylsilyl and acetyl, comprising:

adding a racemic lactam I to an enzyme selected from the group consisting of a hydrolase of Pseudomonas species in buffer, solvent, or a mixture thereof, to obtain an optically enriched compound of the formula Ib

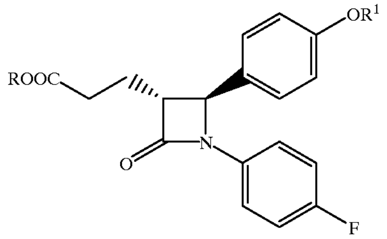
(3R,4S)-Ib
wherein R and $R^1$ are as defined above; and
hydrolysing the carboxylic acid ester of formula Ib to obtain a compound of formula IIa
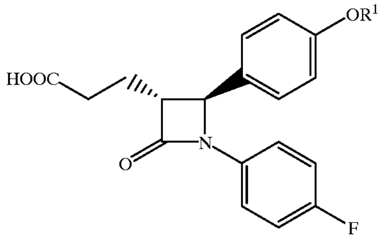
(3R,4S)-IIa
wherein $R^1$ is as defined above.
* * * * *